US012670745B2

(12) United States Patent
Lee et al.

(10) Patent No.: US 12,670,745 B2
(45) Date of Patent: Jun. 30, 2026

(54) METHOD AND APPARATUS FOR TRAINING NEURAL NETWORK FOR GENERATING DEFORMED FACE IMAGE FROM FACE IMAGE, AND STORAGE MEDIUM STORING INSTRUCTIONS TO PERFORM METHOD FOR GENERATING DEFORMED FACE IMAGE FROM FACE IMAGE

(71) Applicant: Suprema Inc., Seongnam-si (KR)

(72) Inventors: Hyogi Lee, Seongnam-si (KR); Byeong Heon Lee, Seongnam-si (KR); Kideok Lee, Seongnam-si (KR)

(73) Assignee: Suprema Inc., Seongnam-si (KR)

( * ) Notice: Subject to any disclaimer, the term of this patent is extended or adjusted under 35 U.S.C. 154(b) by 294 days.

(21) Appl. No.: 18/491,208

(22) Filed: Oct. 20, 2023

(65) Prior Publication Data

US 2025/0054333 A1     Feb. 13, 2025

(30) Foreign Application Priority Data

Aug. 8, 2023     (KR) ......................... 10-2023-0103334

(51) Int. Cl.
*G06T 11/00* (2026.01)
*G06T 9/00* (2006.01)
(Continued)

(52) U.S. Cl.
CPC .............. *G06V 40/171* (2022.01); *G06T 9/00* (2013.01); *G06T 11/00* (2013.01); *G06V 10/764* (2022.01); *G06V 10/82* (2022.01); *G16H 70/40* (2018.01)

(58) Field of Classification Search
CPC .... G06V 40/171; G06V 10/764; G06V 10/82; G06V 10/774; G06V 40/168; G06T 9/00;
(Continued)

(56) References Cited

U.S. PATENT DOCUMENTS

2020/0397306 A1 * 12/2020 Frank ......................... G01J 5/10
2021/0224993 A1 * 7/2021 Tian ......................... G06N 3/045
2024/0273724 A1 * 8/2024 Koukiou ................... G01J 5/48

FOREIGN PATENT DOCUMENTS

KR     10-2019-0076842 A     7/2019

OTHER PUBLICATIONS

Zein, H., Laurent, L., Fournier, R., & Nait-Ali, A. (Apr. 12, 2023). Generation of artificial facial drug abuse images using deep de-identified anonymous dataset augmentation through Genetics Algorithm (3DG-GA). arXiv.org. https://arxiv.org/abs/2304.06106 (Year: 2023).*

(Continued)

*Primary Examiner* — John Villecco
*Assistant Examiner* — Kyla Guan-Ping Tiao Allen
(74) *Attorney, Agent, or Firm* — Bridgeway IP Law Group, PLLC; Jihun Kim

(57) ABSTRACT

There is provided a method for training a neural network for generating a deformed face image from a face image preformed by an apparatus including a memory and a processor. The method comprises acquiring a face image for training; extracting facial feature information from the face image for training; and training the neural network to generate a deformed face image on the basis of the facial feature information, wherein the training includes generating multiple facial feature information that is gradually changed depending on the dosage or use duration of drugs, using the facial feature information as input data for training.

8 Claims, 6 Drawing Sheets

130

(51) Int. Cl.

| | |
|---|---|
| *G06V 10/764* | (2022.01) |
| *G06V 10/82* | (2022.01) |
| *G06V 40/16* | (2022.01) |
| *G16H 70/40* | (2018.01) |

(58) Field of Classification Search
CPC ................... G06T 11/00; G06T 3/4046; G06T 2207/20081; G06T 2207/20084; G06T 2207/30201; G06T 3/10; G16H 70/40; G06N 3/0475; G06N 3/08
See application file for complete search history.

(56) References Cited

OTHER PUBLICATIONS

Gnanasekar, S., & Yanushkevich, S. (Jul. 2019). Face attributes and detection of drug addicts | IEEE conference publication | IEEE Xplore. IEEE. https://ieeexplore.ieee.org/document/8806203/ (Year: 2019).*

Li, Y., Yan, X., Zhang, B., Wang, Z., Su, H., & Jia, Z. (2021). A Method for Detecting and Analyzing Facial Features of People with Drug Use Disorders. Diagnostics, 11(9), 1562. https://doi.org/10.3390/diagnostics11091562 (Year: 2021).*

Willoughby, C., Banatoski, I., Roberts, P., & Agu, E. (2019). DrunkSelfie: Intoxication detection from smartphone facial images. 2019 IEEE 43rd Annual Computer Software and Applications Conference (COMPSAC), 496-501. https://doi.org/10.1109/compsac.2019.10255 (Year: 2019).*

Elham Farazdaghi et al., "Face Aging Predictive Model due to Methamphetamine Addiction", 2016 International Conference on Bio-engineering for Smart Technologies (BioSMART), Dec. 2016.

Xun Huang et al., "Stacked Generative Adversarial Networks", Proceedings of the IEEE Conference on CVPR, pp. 5077-5086, 2017.

Guangzhen Liu et al., "InsightGAN: Semi-Supervised Feature Learning with Generative Adversarial Network for Drug Abuse Detection", ICONIP 2018, LNCS 11303, pp. 411-422, Dec. 13, 2018.

* cited by examiner

120

130

RANDOM
FACE IMAGE

GENERATOR
NEURAL NETWORK

DEFORMED
FACE IMAGE

METHOD AND APPARATUS FOR TRAINING NEURAL NETWORK FOR GENERATING DEFORMED FACE IMAGE FROM FACE IMAGE, AND STORAGE MEDIUM STORING INSTRUCTIONS TO PERFORM METHOD FOR GENERATING DEFORMED FACE IMAGE FROM FACE IMAGE

TECHNICAL FIELD

The present disclosure relates to artificial intelligence technology, and more particularly, to the field of machine learning for generating a face image.

This work was supported by the Korea Internet & Security Agency grant funded by the Korea government (MSIT) (Project unique No.: 2023160000, and Research Project Title: Development of a High-Performance Embedded Face Recognition Module Based on Cross-Recognition Technology for Heterogeneous Cameras).

CROSS-REFERENCE TO RELATED APPLICATIONS

This application claims priority from Korean Patent Application No. 10-2023-0103334, filed on Aug. 8, 2023, in the Korean Intellectual Property Office, which is incorporated herein by reference in its entirety.

BACKGROUND

Face image generating technology using artificial intelligence has shown significant advancement to the extent of generating a real face in a high resolution, and technology for accurately identifying a face by extracting face-image feature information is also being researched in a variety of ways.

On the other hand, drug-related crimes are rapidly increasing domestically and internationally, and national agencies in various countries are making efforts to eradicate drug-related crimes. Nevertheless, teenagers or individuals in their twenties tend to be easily exposed to drugs, and their awareness of the risks caused by drugs is relatively low compared to other age groups.

In overseas countries, the human rights of criminals are low, so their personal information is often made public. It is necessary to accurately determine whether drugs are taken by more actively using the personal information of the drug criminals and to previously recognize the risks of drug crimes.

The above-described background is technical information that is possessed by the inventor for deriving the present disclosure or acquired in the process of deriving the present disclosure, and cannot be necessarily said to be technology known to the general public before filing the present disclosure.

SUMMARY

In view of the above, the present disclosure provides a face image generation technology that can generate a face changed when taking drugs from the face of an ordinary person using a deep learning-based face generating algorithm.

The aspects of the present disclosure are not limited to the foregoing, and other aspects not mentioned herein will be clearly understood by those skilled in the art from the following description.

In accordance with an aspect of the present disclosure, there is provided a method for training a neural network for generating a deformed face image from a face image preformed by an apparatus including a memory and a processor, the method comprises: acquiring a face image for training; extracting facial feature information from the face image for training; and training the neural network to generate a deformed face image on the basis of the facial feature information, wherein the training includes generating multiple facial feature information that is gradually changed depending on the dosage or use duration of drugs, using the facial feature information as input data for training.

The multiple facial feature information may include at least one level information on the basis of an amount of change in face image, and the generating the multiple facial feature information may include providing an output of preceding multiple facial feature information of the level information as an input of following multiple facial feature information of the level information.

The training the neural network may include decoding the multiple facial feature information to output multiple face images for each level.

The neural network may include a generator and a discriminator in a generative adversarial network (GAN).

The training the neural network may include training the generator to generate a fake face image multiplexed for each level when the face image is input; and training the discriminator to classify the fake face image when the fake face image generated by the generator is input.

The training the generator may include receiving a discrimination result output from the discriminator and training the generator to generate the fake face image.

The drugs may include addictive drugs, and the addictive drugs include narcotic drugs.

The acquiring the face image for training may include acquiring face images of a plurality of pre-established drug criminals, as the face image for training, and the extracting the facial feature information includes classifying a deformation degree of each face image of the plurality of drug criminals into levels.

The classifying may include determining the face image for training for extracting the facial feature information on the basis of the priority or average value of results obtained by classifying the deformation degree into levels.

The acquiring the face image may include converting the face image for training into a near infrared ray (NIR) face image for training, and the extracting the facial feature information includes extracting facial feature information from the NIR face image for training.

In accordance with another aspect of the present disclosure, there is provided an image generating apparatus for training a neural network for generating a deformed face image from a face image, the apparatus comprises: a storage medium storing one or more instructions; an acquisition unit acquiring a face image for training; and a processor executing the one or more instructions stored in the storage medium, wherein the instructions, when executed by the processor, cause the processor to extract facial feature information from the face image for training, and train the neural network to generate the deformed face image, on the basis of the facial feature information, wherein the processor is configured to generate multiple facial feature information that is gradually changed depending on the dosage or use duration of drugs, on the basis of the facial feature information.

The multiple facial feature information may include at least one level information on the basis of an amount of change in face image.

The processor may be configured to provide an output of preceding multiple facial feature information of the level information as an input of following multiple facial feature information of the level information.

The processor may be configured to decode the multiple facial feature information to output multiple face images for each level.

The neural network may include a generator and a discriminator in a generative adversarial network. The processor may be configured to train the generator to generate a fake face image multiplexed for each level when the face image for training is input, and train the discriminator to classify the fake face image when the fake face image generated by the generator.

The processor may be configured to receive a discrimination result output from the discriminator and train the generator to generate the fake face image.

The acquisition unit may be configured to acquire face images of a plurality of pre-established drug criminals, and classify a deformation degree of each face image of the plurality of drug criminals into levels.

The acquisition unit may be configured to determine the face image for training for extracting the facial feature information on the basis of the priority or average value of results obtained by classifying the deformation degree into levels.

The acquisition unit may be configured to convert the face image for training into a near infrared ray face image for training, and the processor may be configured to extract facial feature information from the NIR face image for training.

In accordance with another aspect of the present disclosure, there is provided a non-transitory computer-readable recording medium storing a computer program, which comprises instructions for a processor to perform a method for generating a deformed face image from a face image, the method comprise: acquiring a face image for training; extracting facial feature information from the face image for training; and generating the deformed face image from the facial feature information using a pre-trained neural network, wherein the deformed face image is generated based on multiple facial feature information that is gradually changed depending on the dosage or use duration of drugs.

The pre-trained neural network may include a generator and a discriminator in a generative adversarial network (GAN). The generator generates the deformed face image depending on the dosage or use duration of drugs when the face image is input; and the discriminator determines usage of drugs or dosage of drugs when the face image is input.

According to embodiments of the present disclosure, a deep learning-based face generating algorithm is used to generate a face changed when taking drugs from the face of an ordinary person, thus informing the risks of narcotic crimes and being useful to create a prediction montage when a drug criminal is missing.

DETAILED DESCRIPTION

Figure 1:
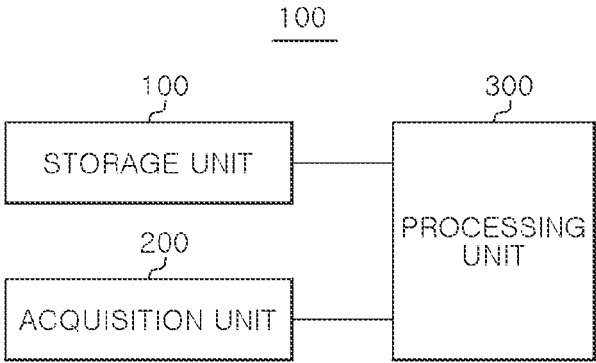
FIG. 1 is a block diagram illustrating an image generating apparatus according to an embodiment of the present disclosure, which trains a neural network for generating a deformed face image from a face image.

The advantages and features of the embodiments and the methods of accomplishing the embodiments will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

Terms used in the present specification will be briefly described, and the present disclosure will be described in detail.

In terms used in the present disclosure, general terms currently as widely used as possible while considering functions in the present disclosure are used. However, the terms may vary according to the intention or precedent of a technician working in the field, the emergence of new technologies, and the like. In addition, in certain cases, there are terms arbitrarily selected by the applicant, and in this case, the meaning of the terms will be described in detail in the description of the corresponding invention. Therefore, the terms used in the present disclosure should be defined based on the meaning of the terms and the overall contents of the present disclosure, not just the name of the terms.

When it is described that a part in the overall specification "includes" a certain component, this means that other components may be further included instead of excluding other components unless specifically stated to the contrary.

In addition, a term such as a "unit" or a "portion" used in the specification means a software component or a hardware component such as FPGA or ASIC, and the "unit" or the "portion" performs a certain role. However, the "unit" or the "portion" is not limited to software or hardware. The "portion" or the "unit" may be configured to be in an addressable storage medium, or may be configured to reproduce one or more processors. Thus, as an example, the "unit" or the "portion" includes components (such as software components, object-oriented software components, class components, and task components), processes, functions, properties, procedures, subroutines, segments of program code, drivers, firmware, microcode, circuits, data, database, data structures, tables, arrays, and variables. The functions provided in the components and "unit" may be combined into a smaller number of components and "units" or may be further divided into additional components and "units".

Hereinafter, the embodiment of the present disclosure will be described in detail with reference to the accompanying drawings so that those of ordinary skill in the art may easily implement the present disclosure. In the drawings, portions not related to the description are omitted in order to clearly describe the present disclosure.

Hereinafter, an embodiment of the present disclosure will be described in detail with reference to the accompanying drawings.

FIG. 1 is a block diagram illustrating an image generating apparatus according to an embodiment of the present disclosure, which trains a neural network for generating a deformed face image from a face image.

As shown in FIG. 1, the image generating apparatus which trains the neural network for generating the deformed face image from the face image may include a storage unit 100, an acquisition unit 200, and a processing unit 300.

Figure 2:
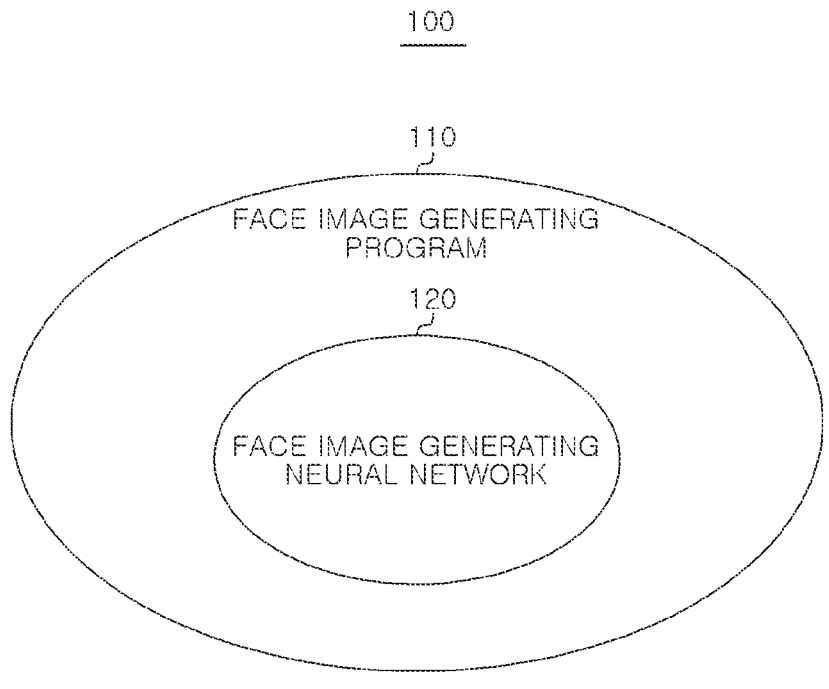
FIG. 2 is a conceptual diagram illustrating a face image generating program included in a storage unit in the image generating apparatus of FIG. 1.

As shown in FIG. 2, the storage unit 100 may store a face image generating program 110 according to an embodiment of the present disclosure, and information required for executing the face image generating program 110. The face image generating program 110 may include a face image generating neural network 120 for a learning function. The face image generating neural network 120 for the learning function will be described in detail with reference to FIGS. 3 to 5.

The acquisition unit 200 may acquire a face image for learning.

The face image for learning acquired through the acquisition unit 200 may include, for example, at least one image of an RGB face image for learning, an infrared ray (IR) face image for learning, and a near infrared ray (NIR) face image for learning. That is, according to the embodiment of the present disclosure, the RGB image may be acquired through the acquisition unit 200 to be used as the face image for learning, and the RGB image may be converted into the IR image or NIR image to be used as the NIR face image for learning. Here, a separate learning process, e.g., a deep learning-based learning process may be required to convert the RGB image into the IR image or NIR image. Such a learning process is an additional feature for implementing the embodiment of the present disclosure, and a detailed description thereof will be omitted herein.

In this way, the face image for learning or the TR/NIR face image for learning acquired through the acquisition unit 200 may be, for example, an image using the face image of an international drug criminal. Thus, the acquisition unit 200 may acquire the face image (or NIR face image) of the international drug criminal, and determine the final face image for learning by classifying the deformation degree of each acquired face image of the drug criminal into levels. The face image for learning acquired and determined through the acquisition unit 200 may be exemplified as shown in Table 1 below.

TABLE 1

| | Drug criminal 1 | Drug criminal 2 | . . . | Drug criminal 99999 | Drug criminal 100000 |
|---|---|---|---|---|---|
| Classifier 1 | Level 3 | Level 1 | | Level 5 | Level 2 |
| Classifier 2 | Level 3 | Level 1 | | Level 5 | Level 4 |
| Classifier 3 | Level 3 | Level 1 | | Level 4 | Level 3 |

TABLE 1-continued

| | Drug criminal 1 | Drug criminal 2 | . . . | Drug criminal 99999 | Drug criminal 100000 |
|---|---|---|---|---|---|
| Classifier 4 | Level 3 | Level 2 | | Level 5 | Level 2 |
| Classifier 5 | Level 4 | Level 1 | | Level 4 | Level 2 |
| Final classifier | Level 3 | Level 1 | | Level 5 | Level 2 |

As shown in Table 1, in the embodiment of the present disclosure, approximately 100,000 face images of drug criminals are used, and the deformation degree for each of the 100,000 face images of drug criminals is classified into a total of five levels.

Further, the acquisition unit 200 may determine the face image having the deformation degree of any one of the five classified levels as the final classifier. For example, in the case of the drug criminal face image 1 in Table 1, the acquisition unit 200 may determine the final face image for learning on the basis of the average value of results classified into a total of five levels. Alternatively, the acquisition unit 200 may determine the final face image for learning on the basis of the priority of the results classified into a total of five levels.

The face image for learning acquired and determined by the acquisition unit 200 may be provided to the processing unit 300. The processing unit 300 may extract facial feature information from the face image for learning acquired and determined through the acquisition unit 200.

When the facial feature information is extracted, the processing unit 300 may train the face image generating neural network 120 for the learning function in the face image generating program 110 of FIG. 2 to generate the deformed face image on the basis of the facial feature information. The deformed face image may include, for example, a face image deformed depending on the dosage or duration of drug use.

Figure 3:
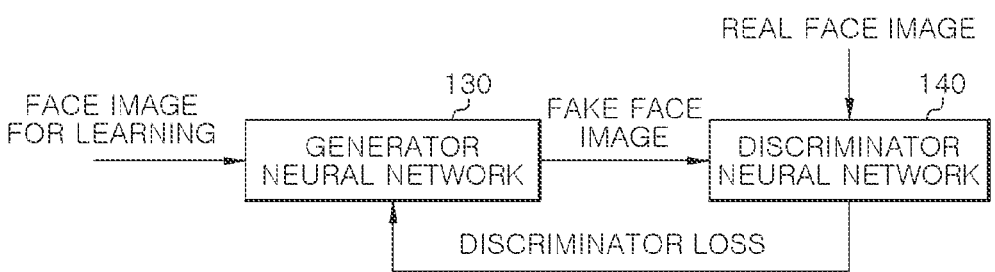
FIG. 3 is a block diagram illustrating the function of the face image generating neural network in the face image generating program of FIG. 2.

As shown in FIG. 3, the face image generating neural network 120 may include a generator neural network 130 and a discriminator neural network 140 within a GAN, which is a generative adversarial neural network.

In FIG. 3, when the generator neural network 130 receives the face image for learning, it may be learned to generate a fake face image for the input face image for learning.

The fake face image of the generator neural network 130 may be provided to the discriminator neural network 140.

The discriminator neural network 140 may be learned to determine whether the fake face image generated by the generator neural network 130 is genuine or false.

The discriminator neural network 140 may generate a discriminator loss to further train the generator neural network 130 and the discriminator neural network 140 itself using the output authenticity.

To this end, the discriminator neural network 140 may further receive a correct answer regarding the authenticity of the fake face image. The discriminator neural network 140 may compare the correct answer regarding the authenticity with real output authenticity, and generate the discriminator loss as the result of the comparison.

That is, the discriminator neural network 140 outputs a value between 0 and 1. As the value output by the discriminator neural network 140 is closer to 0, the input fake image may be determined to be false. As the value output is closer to 1, the input fake image may be determined to be genuine. For example, for the input fake image, when the discriminator neural network 140 outputs 0.7 and the correct answer for determining the authenticity is genuine (1), 0.3 (=1–0.7) may be determined as the discriminator loss.

Therefore, the discriminator neural network 140 may transmit the discriminator loss as feedback data for further learning the generator neural network 130 and the discriminator neural network 140 to the generator neural network 130 and input it back to the discriminator neural network 140 itself.

The generator neural network 140 may be adjusted not to generate the fake image due to the characteristics of the generative adversarial neural network. Due to the discriminator loss, the generator neural network 140 may generate only a normal face image.

Herein, for the convenience of description, it is described that the image generating apparatus not only generates the face image but also performs learning to generate the face image, but the present disclosure is not limited thereto. That is, according to an embodiment, the face image generating neural network 120 may be learned by apparatus other than the image generating apparatus.

Meanwhile, the generator neural network 130 according to an embodiment of the present disclosure is learned to generate the fake face image "multiplexed for each level" for the facial feature information of the face image for learning.

Figure 4:
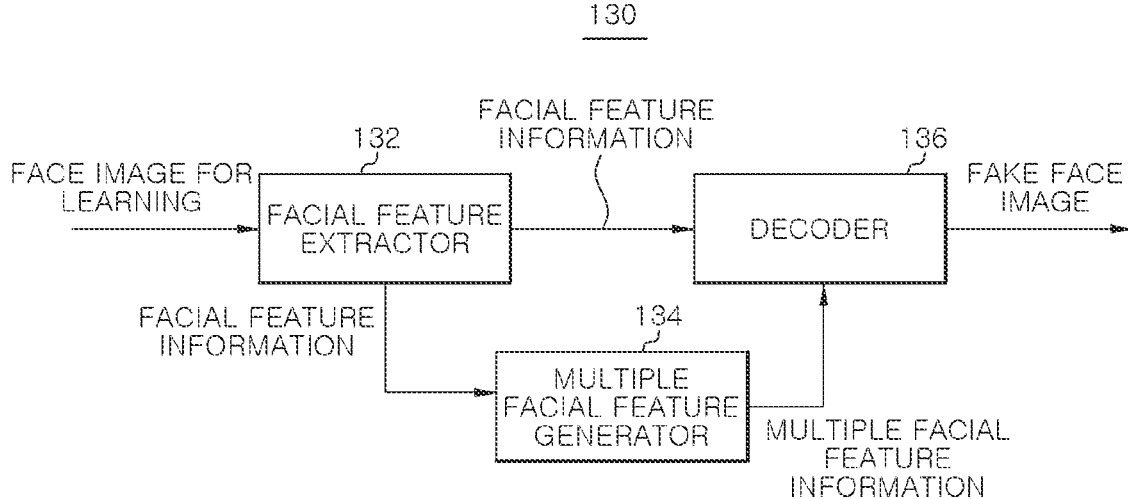
FIG. 4 is a block diagram illustrating the function of a generator neural network in the face image generating neural network of FIG. 3.

FIG. 4 is a block diagram illustrating the function of the generator neural network 130.

As shown in FIG. 4, the generator neural network 130 according to an embodiment of the present disclosure may include a facial feature extractor 132, a multiple facial feature generator 134, and a decoder 136.

The facial feature extractor 132 may extract the facial feature information from the face image for learning. The facial feature information may be extracted using various feature extraction techniques, and there is no need to be limited to a specific technique.

The facial feature information extracted by the facial feature extractor 132 may be provided to the multiple facial feature generator 134 formed of multiple networks.

The multiple facial feature generator 134 may generate a deformed face image on the basis of the extracted facial feature information. According to an embodiment of the present disclosure, the multiple facial feature generator 134 generates multiple facial feature information that is gradually changed depending on the dosage or duration of drug use. The multiple facial feature information is the multiple facial feature information about the face image for learning obtained through the acquisition unit 200, that is, the face image for learning that is finally determined by classifying the deformation degree of each of the acquired face images of drug criminals into levels, and may include at least one level information on the basis of the amount of change in face image.

Figure 5:
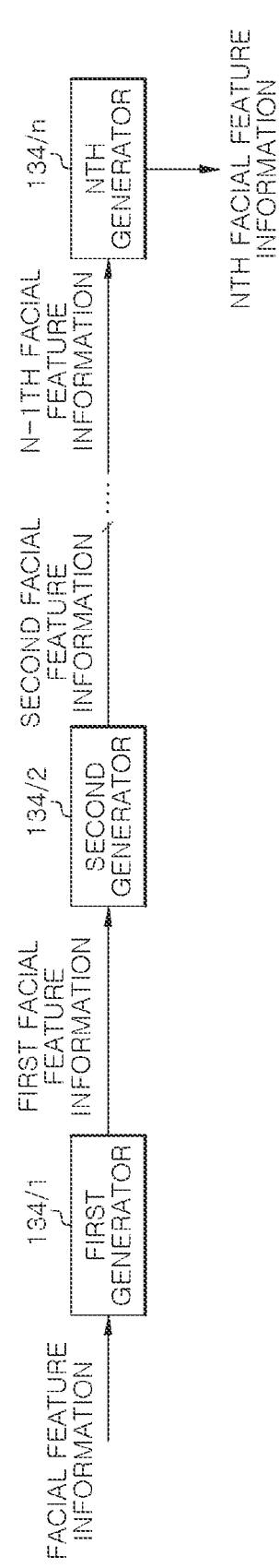
FIG. 5 is a block diagram illustrating the specific function of a multiple facial feature generator in the generator neural network of FIG. 4.

FIG. 5 is a block diagram illustrating the specific function of the multiple facial feature generator 134 of FIG. 4.

As shown in FIG. 5, the multiple facial feature generator 134 may include first to nth generators 134/1 to 134/n. That is, the multiple facial feature generator 134 according to an embodiment of the present disclosure may be composed of multiple networks and be implemented to generate facial feature information that is gradually changed by considering continuity between target levels. The multiplexing configuration of the multiple facial feature generator 134 may vary depending on system environment or required specifications.

First, the first generator 134/1 may output a primary deformed face image, i.e., primary deformed first facial feature information, from the input facial feature information.

The second generator 134/2 may receive the first facial feature information of the first generator 134/1, and output a secondary deformed face image, i.e., secondary deformed second facial feature information.

The subsequent input/output operations may proceed in the same manner. The nth generator 134/n at a final stage may receive the n-1th facial feature information, and output nth deformed nth facial feature information, thereby outputting final multiple facial feature information. In this way, by setting the output value at an output stage of each generator as an input value at an input stage of each generator, continuity across levels may be guaranteed when generating the facial feature information for each level.

The decoder 136 may decode the multiple facial feature information that is finally output through the multiple facial feature generator 134, and output multiple face images for each level.

Figure 6:
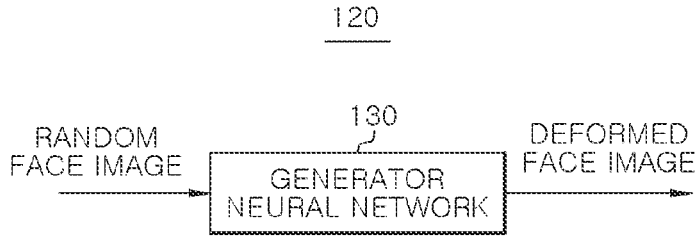
FIG. 6 is an example diagram illustrating an image generating apparatus according to an embodiment of the present disclosure, for generating a deformed face image from a face image.

FIG. 6 is an example diagram illustrating the image generating apparatus according to an embodiment of the present disclosure, specifically the face image generating neural network 120 that may be included in the face image generating apparatus for generating the deformed face image from the face image.

The image generating apparatus for generating the deformed face image has the same configuration as the image generating apparatus that trains the neural network for generating the deformed face image described in FIG. 1, and has the functional feature generating the deformed face image through the generator neural network 130 in the face image generating neural network when a random face image is input.

To this end, the face image generating apparatus for generating the deformed face image from the face image according to an embodiment of the present disclosure may include the storage unit 100 that stores the face image generating program 110, the acquisition unit 200 that acquires the face image, and the processing unit 300 that extracts the facial feature information from the acquired face image and generates the deformed face image from the facial feature information using previously trained face image generating neural network 120 in the face image generating program.

Here, the face image acquired through the acquisition unit 200 may include, for example, at least one image of the RGB face image, the IR face image, and the NIR face image. That is, according to the embodiment of the present disclosure, the RGB image may be acquired through the acquisition unit 200 to generate the deformed face image, and the RGB image may be converted into the IR image or NR image to generate the deformed face image.

Further, the deformed face image may be generated on the basis of the multiple facial feature information that is gradually changed depending on the dosage or use duration of drugs (e.g., addictive drugs such as narcotics).

Therefore, according to an embodiment of the present disclosure, it is possible to generate the deformed face image for the general RGB image as well as the IR image or NIR image based on the RGB image. Thus, it is possible to efficiently and reliably predict the face images of drug criminals or face images recognized at night.

The face image generating neural network 120 may include the generator neural network 130. When a random face image is input from the outside through the generator neural network 130, the processing unit 300 may perform processing to generate the face image deformed by drugs (e.g., addictive drugs such as narcotics). Thereby, according to an embodiment of the present disclosure, by inputting a normal face, the face deformed by drugs may be easily predicted, and the risks of addictive drugs such as narcotics may be shared or recognized.

Meanwhile, the face image generating neural network 120 of the image generating apparatus may include the discriminator neural network 140. When a random face image is input from the outside through the discriminator neural network 140, the processing unit 300 may perform processing to determine the usage of drugs or dosage of drugs (e.g., addictive drugs such as narcotics). Thereby, according to an embodiment of the present disclosure, when inputting a normal face, it is possible to easily determine whether drugs are taken or the degree of drug use. Accordingly, the face of a drug criminal can be predicted or recognized.

As described above, according to an embodiment of the present disclosure, a deep learning-based face generating algorithm, e.g. GAN is used to generate a face that changes when taking drugs from the face of an ordinary person, thus informing the risks of narcotic crimes and being useful to create a prediction montage when a drug criminal is missing.

Combinations of steps in each flowchart attached to the present disclosure may be executed by computer program instructions. Since the computer program instructions can be mounted on a processor of a general-purpose computer, a special purpose computer, or other programmable data processing equipment, the instructions executed by the processor of the computer or other programmable data processing equipment create a means for performing the functions described in each step of the flowchart. The computer program instructions can also be stored on a computer-usable or computer-readable storage medium which can be directed to a computer or other programmable data processing equipment to implement a function in a specific manner. Accordingly, the instructions stored on the computer-usable or computer-readable recording medium can also produce an article of manufacture containing an instruction means which performs the functions described in each step of the flowchart. The computer program instructions can also be mounted on a computer or other programmable data processing equipment. Accordingly, a series of operational steps are performed on a computer or other programmable data processing equipment to create a computer-executable process, and it is also possible for instructions to perform a computer or other programmable data processing equipment to provide steps for performing the functions described in each step of the flowchart.

In addition, each step may represent a module, a segment, or a portion of codes which contains one or more executable instructions for executing the specified logical function(s). It should also be noted that in some alternative embodiments, the functions mentioned in the steps may occur out of order. For example, two steps illustrated in succession may in fact be performed substantially simultaneously, or the steps may sometimes be performed in a reverse order depending on the corresponding function.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. An apparatus for training a neural network for generating a deformed face image from a face image, the apparatus comprising:
   a storage medium configured to store one or more instructions;
   an acquisition unit configured to acquire a face image for training; and
   a processor configured to execute the one or more instructions stored in the storage medium, wherein the one or more instructions, when executed by the processor, cause the processor to extract a facial feature information from the face image for training, and train the neural network to generate the deformed face image, on a basis of the facial feature information,
   wherein the processor is configured to generate multiple facial feature information that is changed depending on a dosage or use duration of drugs, on the basis of the facial feature information.

2. The apparatus of claim 1,
   wherein the multiple facial feature information includes at least one level information that is based on an amount of face image change, and
   wherein the processor is configured to provide an output of preceding multiple facial feature information of the at least one level information as an input of following multiple facial feature information of the at least one level information.

3. The apparatus of claim 2,
   wherein the processor is configured to decode the multiple facial feature information to output multiple face images for each level.

4. The apparatus of claim 1,
   wherein the neural network includes a generator and a discriminator in a generative adversarial network, and
   wherein the processor is configured to train the generator to generate a fake face image multiplexed for each level when the face image for training is input, and train the discriminator to classify the fake face image when the fake face image generated by the generator.

5. The apparatus of claim 4,
   wherein the processor is configured to receive a discrimination result output from the discriminator and train the generator to generate the fake face image.

6. The apparatus of claim 1,
   wherein the acquisition unit is configured to acquire face images of a plurality of drug criminals, and classify a deformation degree of each face image of the plurality of drug criminals into levels.

7. The apparatus of claim 6,
   wherein the acquisition unit is configured to determine the face image for training for extracting the facial feature information based on a priority or average value of results obtained by classifying the deformation degree into levels.

8. The apparatus of claim 1,
   wherein the acquisition unit is configured to convert the face image for training into a near infrared ray face image for training, and wherein the processor is configured to extract facial feature information from the near infrared ray face image for training.

* * * * *